(12) United States Patent
Yamazaki et al.

(10) Patent No.: US 6,904,614 B2
(45) Date of Patent: Jun. 14, 2005

(54) GLOVE WITH ELECTRODES

(75) Inventors: Iwao Yamazaki, Tokyo (JP); Akitsugu Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 91 days.

(21) Appl. No.: 10/415,594

(22) PCT Filed: Nov. 11, 2002

(86) PCT No.: PCT/JP02/11700
§ 371 (c)(1),
(2), (4) Date: Apr. 30, 2003

(87) PCT Pub. No.: WO03/088776
PCT Pub. Date: Oct. 30, 2003

(65) Prior Publication Data
US 2004/0237170 A1 Dec. 2, 2004

(30) Foreign Application Priority Data
Apr. 19, 2002 (JP) ........................................ 2002-118352

(51) Int. Cl.[7] .............................................. A41D 19/00
(52) U.S. Cl. .......................................... 2/159; 2/161.6
(58) Field of Search ........................... 2/158, 159, 160, 2/161.6, 161.7, 163; 361/232, 230; 128/639, 644, 799, 802, 803; 607/76, 48, 50, 115

(56) References Cited

U.S. PATENT DOCUMENTS

| | | | | | |
|---|---|---|---|---|---|
| 206,474 | A | * | 7/1878 | Morel | 601/15 |
| 4,370,696 | A | * | 1/1983 | Darrell | 361/232 |
| 4,485,426 | A | * | 11/1984 | Kerls | 361/232 |
| 4,510,939 | A | * | 4/1985 | Brenman et al. | 600/384 |
| 4,729,377 | A | * | 3/1988 | Granek et al. | 600/393 |
| 5,070,862 | A | * | 12/1991 | Berlant | 601/21 |
| 6,584,359 | B1 | * | 6/2003 | Motoi | 607/76 |

FOREIGN PATENT DOCUMENTS

| | | | |
|---|---|---|---|
| JP | 61-164211 | 10/1986 | |
| JP | 62-158388 | 10/1987 | |
| JP | 3-233391 | * 3/1991 | ............ G01V/3/08 |
| JP | 5-91693 | 12/1993 | |
| JP | 3002938 | 7/1994 | |
| JP | 7-194711 | 8/1995 | |
| JP | 3040632 | 6/1997 | |
| JP | 2001-198227 | 7/2001 | |

* cited by examiner

Primary Examiner—Gary L. Welch
(74) Attorney, Agent, or Firm—Finnegan, Henderson, Farabow, Garrett & Dunner, L.L.P.

(57) ABSTRACT

A glove with electrodes comprises a pair of flat electrodes 3, 4 which are disposed with a space therebetween on the surface of the palm side of a glove body 2 which is made of an electrical insulating material, an operation panel 30 which is fitted in the vicinity of the wrist on the back or the palm of the glove body 2 to control to supply electricity to the flat electrodes 3, 4, and lead wires 5, 6 which are fitted to the glove body 2 and electrically connect output terminals 40 of the operation panel 30 and the respective flat electrodes 3, 4. The respective flat electrodes 3, 4 are touched with a little space between them to a portion of the human body, and a current is passed to the portion for treatment. Thus, the glove body 2 can be put on one hand only to easily treat from a wide area to a small portion by passing a current to any portion of the human body.

13 Claims, 4 Drawing Sheets

GLOVE WITH ELECTRODES

TECHNICAL FIELD

The present invention relates to a glove with electrodes, which is used to treat by passing a weak current to the electrodes contacted to a desired portion of the human body so to electrically stimulating the outside portion.

BACKGROUND ART

Conventionally, there is generally used a pulse health appliance which performs treatments such as stimulation of muscles (EMS: electrical muscle stimulation), promotion of a flow of lymph, a recovery from fatigue, and the like by contacting electrodes to a desired portion of the human body and passing a weak pulse current to the electrodes.

Such a pulse health appliance is known having various types of electrode shapes depending on a treating method, an object portion and the like, and there is also proposed a pulse health appliance which has electrodes respectively attached to the palms of a pair of gloves and connected to a control section including a power supply through wiring. Such gloves with electrodes are put on both hands and touched with a space between them to a portion to be treated, and a weak current is passed between the electrodes disposed on the respective gloves to perform treatments.

DISCLOSURE OF THE INVENTION

The above-described conventional gloves with electrodes had a problem that it was difficult to treat a portion which was hardly accessed by both hands.

When a very small and limited portion, e.g., a portion of crow's feet, is treated, there was a problem that the treating operation was hard because it was necessary to operate the electrodes of both gloves.

Besides, because both hands are covered with the gloves, there was also a safety problem that it was difficult to operate a switch or the like so to switch the operation modes to make an emergency stop, or the like.

The present invention was achieved in order to remedy the above problems of the existing gloves with electrodes, and it is an object of the present invention to provide a glove with electrodes, which was remedied the above-described operational and safety problems by disposing a pair of electrodes on the surface of the palm side of a single glove to make it possible to perform a treating operation by a single hand.

In order to achieve the above object, a glove with electrodes of the present invention comprises a glove body which is made of an electrical insulating material; a pair of electrodes which are disposed with a space between them on the surface of the palm side of the glove body; an operation panel which is fitted near the wrist on the back or the palm of the glove body to control the supply of a current to the electrodes; and lead wires which are fitted to the glove body to electrically connect the output terminals of the operation panel and the respective electrodes.

The pair of electrodes are desired to have one of them disposed on a bulge portion expanded from the root of the thumb of the glove body and the other of them disposed on at least the fingertips excepting the thumb of the glove body. When the electrodes are disposed as described above, one of the electrodes, which is positioned on the bulge portion expanded from the root of the thumb of the operating hand, is touched to the skin of the portion to be treated, and the other electrode on the pad of at least one fingertip excepting the thumb is touched to a portion a little away from the former portion to perform the treatment. At this time, the electrode having the bulge portion expanded from the root of the thumb is touched to the skin of the portion to be treated, so that the operating hand becomes stable as a whole. And, because the other electrode is disposed on the fingertip which can make fine operations with ease, a small area can also be treated easily. The electrode disposed on the fingertip may be disposed on all of the fingertips or may be disposed on any desired finger.

The electrodes used for the present invention may be any type of flexible conductive material and not limited to a particular type. But, it is suitable to use conductive woven cloth, which is produced by weaving conductive fibers having the surfaces coated with conductive metal such as silver and electrical insulating fibers at an appropriate ratio, because it is good in flexibility and durability.

The glove body is suitably formed of an ordinary thin cloth for gloves but may be made of any glove material as far as it is an electrical insulating material with good operability.

The above electrodes are fixed to the glove body with a hot-melt adhesive agent or by sewing. The operation panel of the present invention is attached to the vicinity of the wrist on the back or the palm of the glove body so that the treatment operation is not disturbed.

The lead wires for connecting the electrodes and the output terminals of the operation panel may be made of a material different from the electrodes but preferably formed of the electrodes by extending them, so that the production process can be reduced, and the number of parts can be decreased.

The operation panel may have its output terminals directly connected to the lead wires but preferably has the electrode terminals fitted to the operation panel side of the lead wires and connected to the output terminals of the operation panel. Especially, when the electrode terminals and the output terminals of the operation panel are configured to have a snap structure so to be detachable freely, it is possible to wash the glove body only. And, to securely fix the operation panel to the glove body, a flat fastener may be disposed on the contact portions of the glove body and the operation panel.

Besides, it is desirable that a power supply such as a battery to supply electricity to the electrodes is built in the operation panel. When the power supply is a battery which has a low output voltage, it may be desirable to include a known step-up device for raising the output voltage because the treatment generally requires a voltage of about 10 to 100V.

According to the present invention, a pair of electrodes are disposed on the surface of the palm of a single glove body. This glove is put on one hand only, and the treatment can be made easily from a wide area to a very small portion by supplying electricity to the required portion of the human body.

BEST MODE FOR CARRYING OUT THE INVENTION

An embodiment of the present invention will be described with reference to the accompanying drawings.

Figure 1:
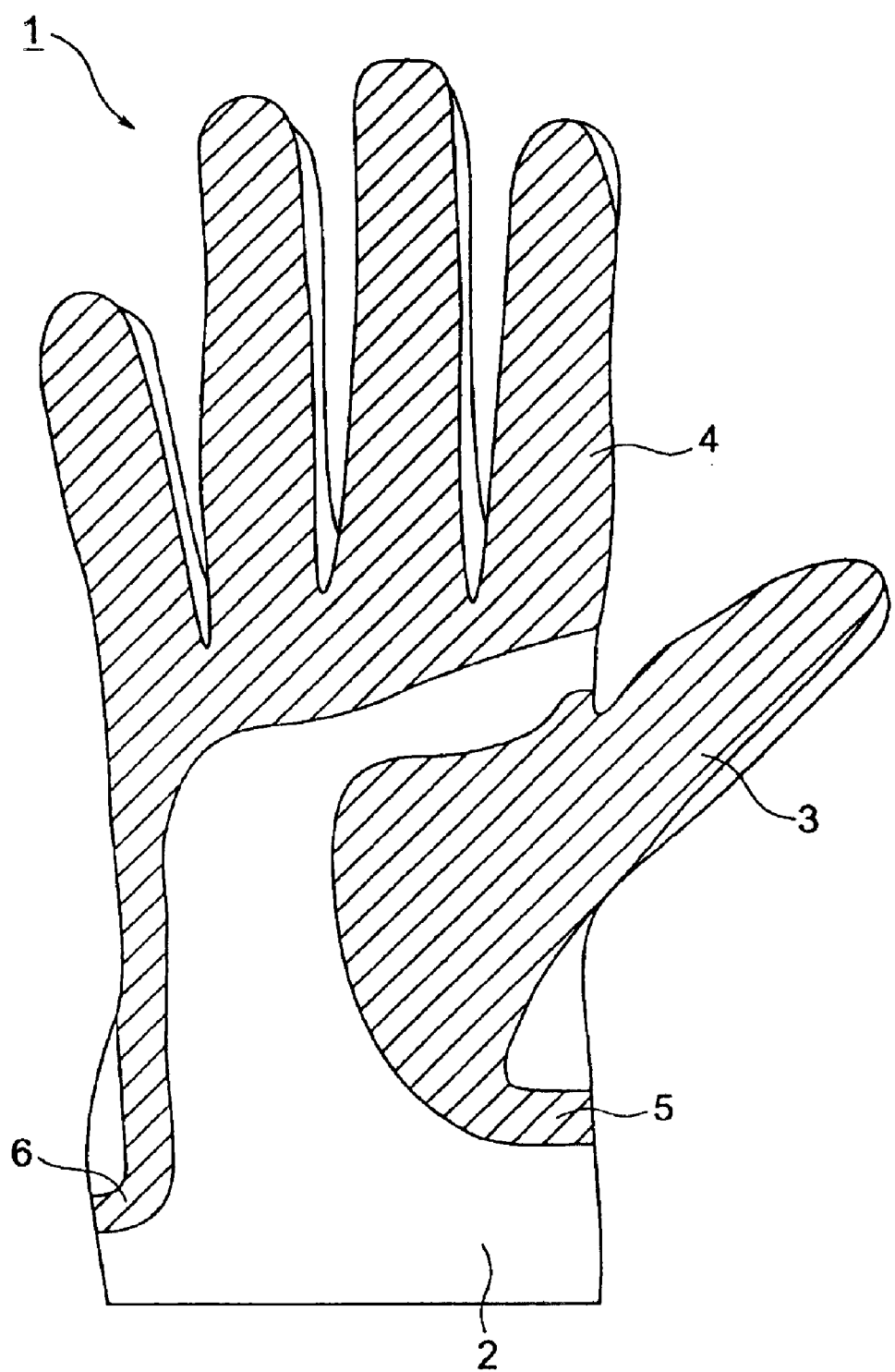
FIG. 1 is a structure diagram showing the palm of a glove with electrodes according to one embodiment of the present invention.
Figure 2:
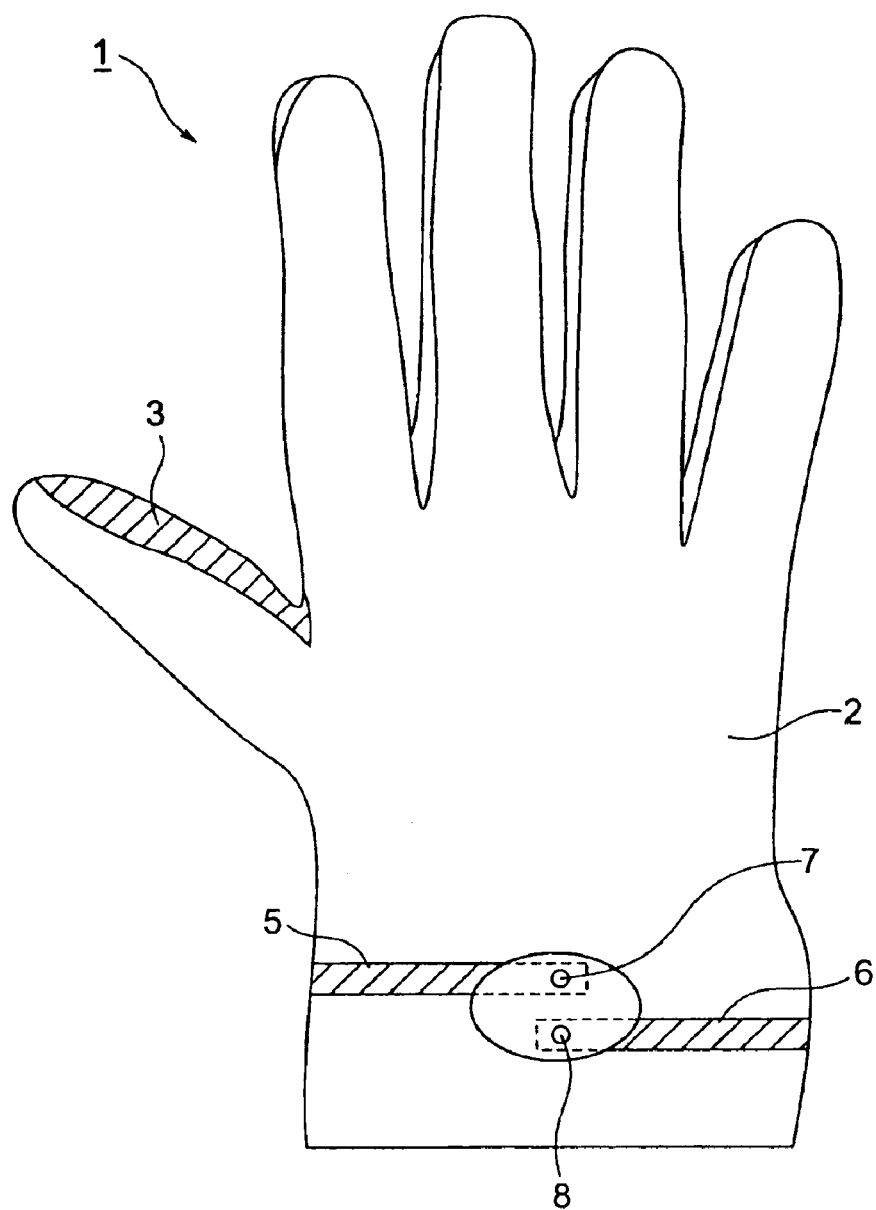
FIG. 2 is a structure diagram showing the back of the glove with electrodes according to one embodiment of the present invention.

One embodiment of the glove with electrodes of the present invention will be described with reference to FIG. 1 to FIG. 3.

As shown in the drawings, a glove with electrodes 1 comprises a glove body 2 which is made of an electrical insulating material, flexible flat electrodes 3, 4 which are fixed to the palm of the glove body 2, an operation panel 30 which supplies electricity to the flat electrodes 3, 4 and controls the operation, and lead wires 5, 6 which electrically connect the operation panel 30 and the flat electrodes 3, 4.

The glove body 2 is made of an electrical insulating material which is thin and good in flexibility, such as synthetic leather, cloth coated with a synthetic resin, or the like, and the thumb and four fingers are independently formed from one another. The glove may have the finger portion formed to have three fingers or as a mitten type.

The flat electrodes 3, 4 and the lead wires 5, 6 are integrally formed of the same conductive cloth. The conductive cloth is formed by weaving about two to five conductive fibers, which have the surfaces of synthetic resin fibers such as polyethylene plated with conductive metal, into ten non-plated electrical insulating fibers. As the conductive metal, nickel, gold, silver, copper or another conductive metal can be used. For the flat electrodes 3, 4, a conductive thin metal plate, a metal laminate film, cloth having a conductive coating such as carbon ink applied on it (carbon printing), a carbon sheet, conductive rubber, silicon or the like can be used.

Then, a process of applying the respective flat electrodes 3, 4 and the lead wires 5, 6 to the glove body 2 will be described.

The flat electrode 3 is disposed to cover from the thumb to the bulge portion expanded from the root of the thumb on the surface of the palm of the glove body 2. This flat electrode 3 has its portion extended as the lead wire 5 to the vicinity of the wrist on the back of the hand, and an electrode terminal 7 for connection with the operation panel 30 is fixed near the end of the extended portion.

The flat electrode 4 is disposed on the four finger cushions excluding the thumb on the palm side of the glove body 2 and extended as the lead wire 6 from the little finger to the vicinity of the wrist on the back side of the hand along the edge of the palm on the little finger side. An electrode terminal 8 for connecting to the operation panel 30 is fixed at the end of the extended portion. The flat electrode 4 may not be applied to all fingers excepting the thumb but may be applied to at least one of them. The electrode terminals 7, 8 are configured to be freely detachable from the output terminals of the operation panel by snap-fastening.

In this embodiment, the flat electrode 3 is a negative electrode and the flat electrode 4 is a positive electrode, but they may be used as reverse polarity. And it is also possible to apply an alternating voltage to them.

The flat electrodes 3, 4 and the lead wires 5, 6 can be sewn as a French seam so that a sewing thread or the like is not exposed to the surface to prevent it from contacting the human skin. The flat electrodes 3, 4 and the lead wires 5, 6 can also be fixed to the glove body 2 with a hot-melt adhesive agent.

Then, control for the operation will be described.

Figure 3A:
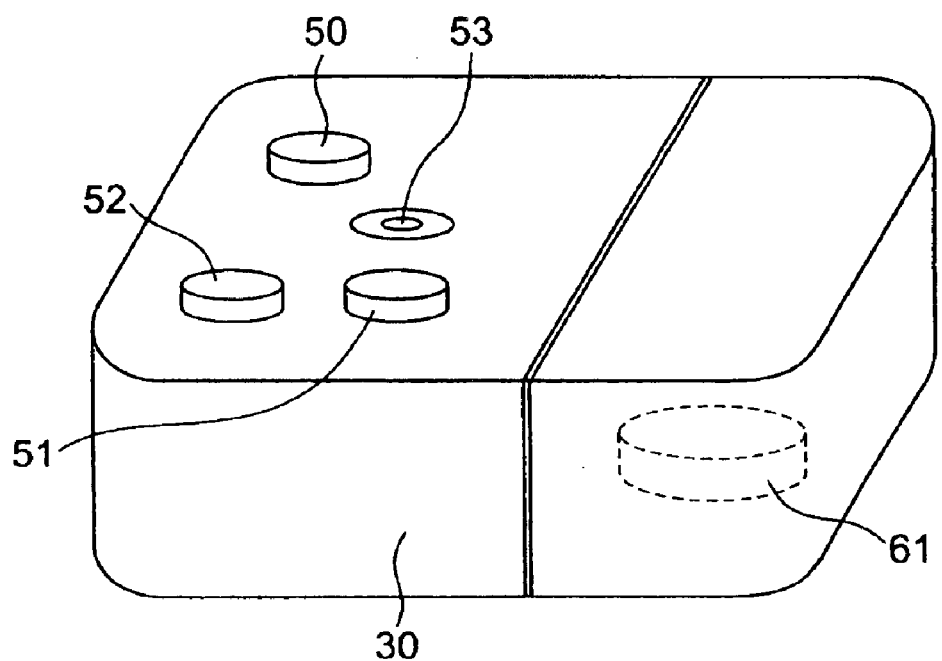
FIG. 3A is a structure diagram showing the front of an operation panel.
Figure 3B:
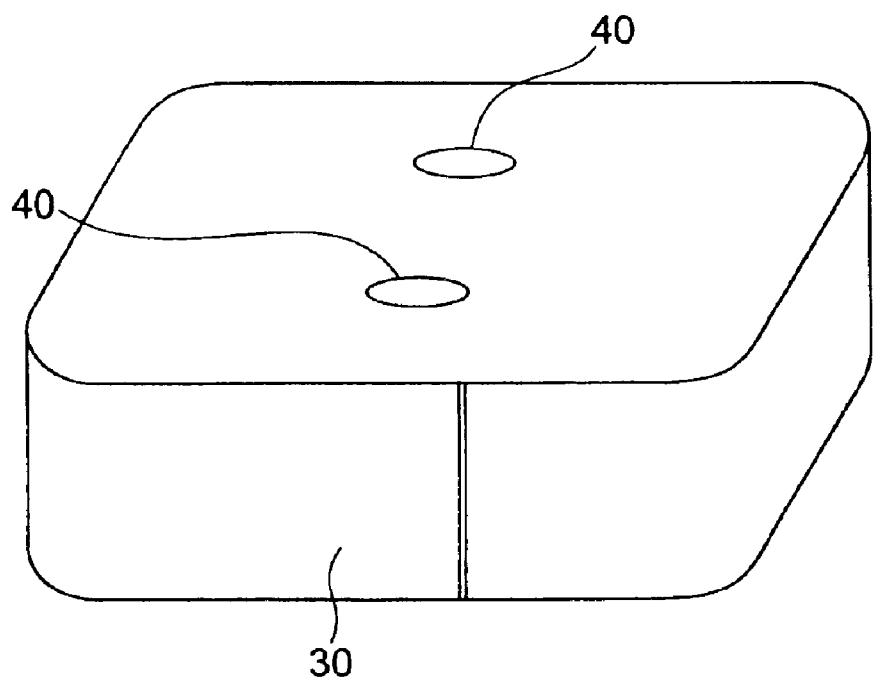
FIG. 3B is a structure diagram showing the back of the operation panel.

For example, a switch 50, a mode switching button 51, an output adjustment button 52, and an operation check lamp 53 are disposed on a surface of the operation panel 30 as shown in FIG. 3. And, output terminals 40, 40 which are connected to the electrode terminals 7, 8 disposed on the lead wires 5, 6 are disposed on the back of the operation panel 30. And, a battery 61 is placed as the power supply in the operation panel 30.

The switch 50 is operated to turn on/off the power supply.

The mode switching button 51 is operated to switch a prescribed mode of pulse voltage to be output. The prescribed mode includes a plurality of patterns with a pulse period of voltage or the like changed.

The output adjustment button 52 is used to adjust the pulse voltage to be output. This adjustment allows determining a treatment such as a comfort mode, a stimulating mode or the like.

For example, the operation check lamp 53 comes on when the switch 50 is on and remains blinking while electrifying to indicate the operation to a user. It is also possible to change the color of light depending on a mode of pulse voltage or to dispose a plurality of lamps for indication.

Figure 4:
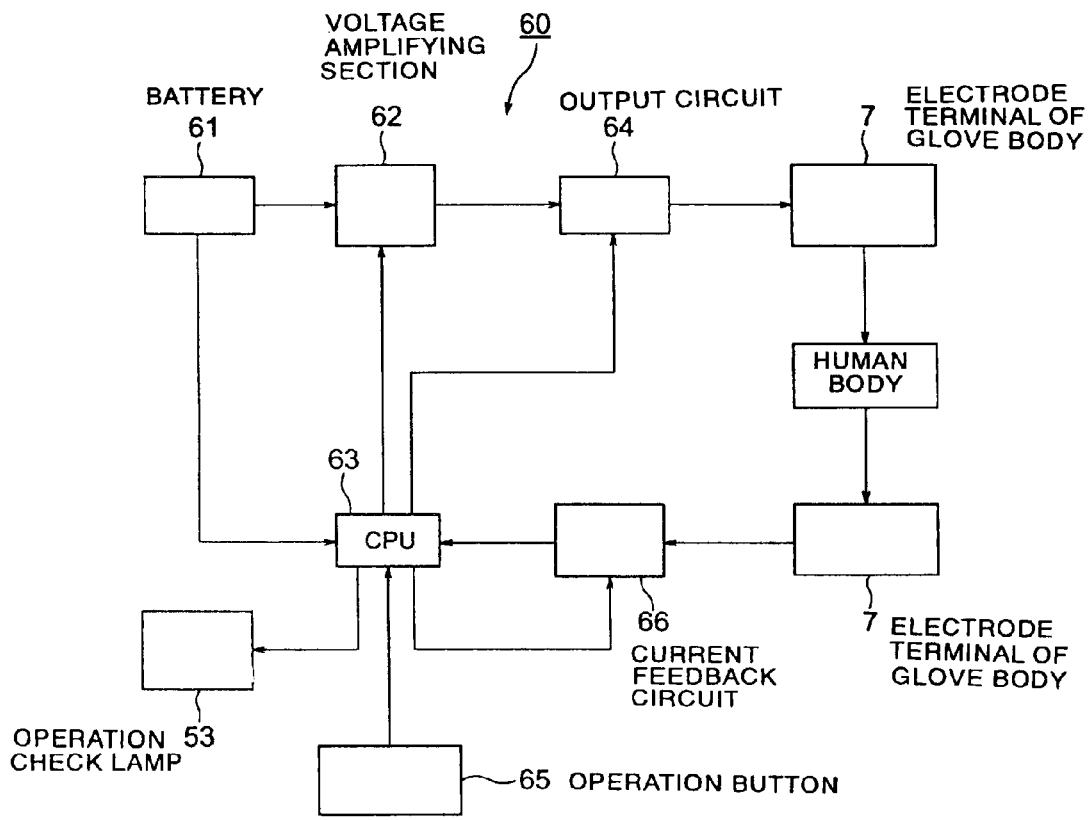
FIG. 4 is a block diagram showing an example of control of the glove with electrodes according to the present invention.

FIG. 4 shows the structure of the control section of the glove with electrodes.

A control device 60 comprises, for example, the battery 61, a CPU 63, a voltage amplifying section 62, an output circuit 64, an operation button 65, and the operation check lamp 53.

The battery 61 may be either a rechargeable battery or a non-rechargeable dry cell.

The voltage amplifying section 62 raises the voltage from the battery 61 by, for example, a step-up device using a coil. And, another device which can raise the voltage can be used other than the step-up device using a coil.

In the output circuit 64, the voltage raised by the voltage amplifying section 62 is subject to pulse control so to output a pulse voltage.

Then, a process of controlling the glove with electrodes 1 will be described.

According to information from the operation button 65 such as the switch 50, the mode switching button 51 or the output adjustment button 52, a signal is output from the CPU 63 to the voltage amplifying section 62, the output circuit 64 or the operation check lamp 53. Based on the information, the voltage amplifying section 62 raises the voltage from the battery 61, and the raised voltage is supplied to the output circuit 64. The output circuit 64 adjusts the output pulse mode of voltage, and the pulse voltage is supplied to the electrode terminal 7 of the glove body 2.

According to the signal from the CPU 63, the operation check lamp 53 comes on or blinks to indicate the operating state.

For example, when no current is passed through a voltage feedback circuit 66 for several seconds, the voltage feedback circuit 66 cuts off the main circuit to stop the main current according to a current feedback control signal from the CPU 63. And, when it is determined by the CPU 63 in about several seconds that the current is passing to the voltage feedback circuit 66, the main circuit of the voltage feedback circuit 66 which was cut off is turned on again according to the current feedback control signal from the CPU 63. And, when the current does not flow for a predetermined period of time, it is controlled to turn off the power supply.

The current feedback control signal is output from the CPU 63 to the voltage feedback circuit 66 to control the voltage feedback circuit 66, so that useless power consumption can be avoided.

Then, one example of actual use of the glove with electrodes will be described.

The operation panel 30 of the glove with electrodes is operated to turn on the power, and the operation mode is determined, so that the glove with electrodes 1 falls in a treatment standby state. Then, the palm side of the glove with electrodes 1 on which the flat electrodes 3, 4 are applied is touched to a portion to be treated. When a small portion is to be treated, the flat electrodes 3, 4 on the thumb and the index finger are touched to it with a small distance between them. Thus, a pulse current flows through and treats the human body by touching as described above. If both the flat electrodes 3, 4 can be touched to a treated portion with a small space between them, it is not limited to the above method of use. If safety can be secured, the glove with electrodes 1 can be put on both hands to treat different portions at the same time.

As described above, the glove with electrodes of the present invention can easily treat from a wide area to a small portion by having a pair of flat electrodes disposed on the surface of the palm side of a single glove body, putting it on one hand only, and passing a current through any portion of the human body. And, because the operation panel having the power supply in it can be removably attached to the body of the glove with electrodes, the glove with electrodes can be used codeless, and the efficiency of work for treatments can be improved. Besides, the switching operation can be performed by one hand because the treatment can be performed by another hand, so that it is easy to switch the operation modes, and the power can be shut off instantly in case of an emergency stop. Thus, safety can be improved.

INDUSTRIAL APPLICABILITY

The glove with electrodes of the present invention can easily treat a portion of the human body by passing a current to it and can be produced commercially.

What is claimed is:

1. A glove for electrical treatment of a human body, comprising:

a glove body made of an electrical insulating material;

a pair of electrodes disposed with a space between them on a surface of a palm side of the glove body, the electrodes being made of conductive woven cloth composed of conductive fibers having a conductive coating on surfaces thereof woven into electrical insulating fibers;

an operation panel fitted near the wrist on a back or the palm side of the glove body to control a supply of a current to the electrodes; and lead wires fitted to the glove body to electrically connect output terminals of the operation panel and the respective electrodes.

2. The glove according to claim 1, wherein the glove body includes a palm, four fingers and a thumb, and wherein one of the electrodes is disposed on a bulge portion expanded from a palm side of a root of the thumb of the glove body, and the other of the electrodes is disposed on a tip of at least one of the four fingers of the glove body.

3. The glove according to claim 1, wherein the conductive coating includes silver.

4. The glove according to claim 1, wherein the electrodes are fixed to the glove body with a hot-melt adhesive agent or by sewing.

5. The glove according to claim 1, wherein the lead wires are formed by extending the electrodes.

6. The glove according to claim 1, wherein the operation panel is connected to the lead wires via electrode terminals.

7. The glove according to claim 1, wherein the operation panel is detachably connected to the electrode terminals.

8. The glove according to claim 1, wherein the operation panel includes a power supply for electrifying the electrodes, a current feedback circuit to receive feedback current from one the output terminals, and a central processing unit to stop the electrifying of the electrodes by the power supply in accordance with a predetermined time during which the feedback current does not flow.

9. The glove according to claim 8, wherein the power supply includes a battery, and the operation panel includes a step-up device for raising the voltage of the battery and electrifying the electrodes.

10. The glove according to claim 1, wherein the conductive woven cloth includes about two to five of the conductive fibers woven into ten of the electrical insulating fibers.

11. The glove according to claim 1, wherein at least one of the electrodes is sewn to the glove body by a thread such that the thread is not exposed to contact the human body.

12. The glove according to claim 11, wherein the at least one electrode is sewn to the glove body as a French seam.

13. The glove according to claim 1, wherein the operational panel includes a current feedback circuit to receive feedback current from one of the output terminals, and a central processing unit to control the current feedback circuit in accordance with the feedback current.

* * * * *